(12) United States Patent
Bean, Jr. et al.

(10) Patent No.: US 12,270,084 B2
(45) Date of Patent: Apr. 8, 2025

(54) INDUCTOR PROPERTY IDENTIFICATION FOR POWER CONVERTERS

(71) Applicant: TEXAS INSTRUMENTS INCORPORATED, Dallas, TX (US)

(72) Inventors: Ronnie Antone Bean, Jr., Lenoir City, TN (US); Benjamin Matthew McCue, Clinton, TN (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 18/678,414

(22) Filed: May 30, 2024

(65) Prior Publication Data

US 2024/0322683 A1  Sep. 26, 2024

Related U.S. Application Data

(63) Continuation of application No. 17/388,245, filed on Jul. 29, 2021, now Pat. No. 12,040,706.

(Continued)

(51) Int. Cl.
| | |
|---|---|
| *H02M 3/155* | (2006.01) |
| *A61K 35/74* | (2015.01) |
| *A61K 39/02* | (2006.01) |
| *A61P 31/04* | (2006.01) |
| *C07K 14/195* | (2006.01) |
| *C12N 1/20* | (2006.01) |
| *C12N 15/74* | (2006.01) |

(Continued)

(52) U.S. Cl.
CPC .............. *C12Q 1/689* (2013.01); *A61K 35/74* (2013.01); *A61K 39/0208* (2013.01); *A61P 31/04* (2018.01); *C07K 14/195* (2013.01); *C12N 1/20* (2013.01); *C12N 15/74* (2013.01); *H02J 7/007* (2013.01); *H02M 1/0009* (2021.05); *H02M 1/083* (2013.01); *H02M 3/155* (2013.01); *A61K 2039/521* (2013.01); *C12Q 2600/158* (2013.01)

(58) Field of Classification Search
CPC .... H02M 3/155; H02M 1/0009; H02M 1/083; H02J 7/007
See application file for complete search history.

(56) References Cited

U.S. PATENT DOCUMENTS

| | | | |
|---|---|---|---|
| 12,040,706 B2 * | 7/2024 | Bean, Jr. | ............. H02M 1/0009 |
| 2014/0049239 A1 | 2/2014 | Labbe | |

(Continued)

*Primary Examiner* — Kyle J Moody
(74) *Attorney, Agent, or Firm* — Charles F. Koch; Frank D. Cimino (57) ABSTRACT

A circuit includes a current sensor circuit having inputs and an output. The current sensor inputs are adapted to be coupled to inductor terminals a power converter. The current sensor circuit includes a tunable time constant circuit coupled between the current sensor inputs and the current sensor output. A time constant control circuit is coupled to a tunable time constant circuit, and is configured to tune the time constant circuit responsive to the current sensor output and another signal representative of inductor current. An adjustable gain circuit has a first input coupled to the current sensor output. A direct current resistance (DCR) control circuit has an output coupled to a second input of the adjustable gain circuit, and the DCR control circuit is configured to provide a gain adjust signal at the output thereof responsive to an average current of the inductor and a current command signal for the power converter.

20 Claims, 8 Drawing Sheets

Related U.S. Application Data

(60) Provisional application No. 63/213,579, filed on Jun. 22, 2021.

(51) Int. Cl.
*C12Q 1/689* (2018.01)
*H02J 7/00* (2006.01)
*H02M 1/00* (2006.01)
*H02M 1/08* (2006.01)
*A61K 39/00* (2006.01)

(56) References Cited

U.S. PATENT DOCUMENTS

2018/0152099 A1  5/2018  Savic
2022/0109507 A1  4/2022  Tanaka

* cited by examiner

INDUCTOR PROPERTY IDENTIFICATION FOR POWER CONVERTERS

CROSS-REFERENCE TO RELATED APPLICATION

This application is a continuation of U.S. application Ser. No. 17/388,245 filed Jul. 29, 2021, which claims priority to U.S. Provisional patent application No. 63/213,579, filed Jun. 22, 2021, all of which are hereby incorporated herein by reference in their entirety.

TECHNICAL FIELD

This disclosure relates to identifying properties of inductors for use with power converters.

BACKGROUND

Power converter circuits, such as switch mode power supplies, can include external inductors. The properties of a given inductor can affect performance of the power converter circuit and, in some examples, prior knowledge of inductor properties may be needed to configure the power converter for operation. In many applications, such prior knowledge is not readily available, which requires some mechanism to detect the inductor properties. Also, inductor properties can change with temperature and age.

SUMMARY

In a described example, a circuit includes a current sensor circuit having inputs and an output. The current sensor inputs are adapted to be coupled to inductor terminals of a power converter. The current sensor circuit includes a tunable time constant circuit coupled between the current sensor inputs and the current sensor output. A time constant control circuit is coupled to a tunable time constant circuit, and is configured to tune the time constant circuit responsive to the current sensor output and another signal representative of inductor current. An adjustable gain circuit has a first input coupled to the current sensor output. A direct current resistance (DCR) control circuit has an output coupled to a second input of the adjustable gain circuit, and the DCR control circuit is configured to provide a gain adjust signal at the output thereof responsive to an average current of the inductor and a current command signal for the power converter.

In another described example, an integrated circuit includes a current sensor having inputs and an output. The current sensor inputs are adapted to be coupled to terminals of an inductor of a power converter circuit. The current sensor includes a tunable time constant circuit coupled between the current sensor inputs and the current sensor output. A time constant control circuit has a first input adapted to be coupled to a high-side terminal of the inductor, and a second input coupled the current sensor output. The output of the time constant control circuit is coupled to the tunable time constant circuit. A gain circuit is in a feedback loop of the power converter circuit. The gain circuit has first and second gain inputs and a gain output, in which the first gain input is coupled to the current sensor output, and the gain output is coupled to at least one input of a switch control circuit of the power converter circuit. A direct current resistance (DCR) control circuit has first, second and third DCR inputs and a DCR output. The first DCR input is coupled to the current sensor output, and the second DCR input is coupled to an output of average inductor current sensor. The third DCR input is coupled to a current command input, and the DCR output is coupled to the second input of the gain circuit.

In a further described example, a system includes a power stage coupled between a power input and a power output. The power stage includes an inductor and a switch circuit coupled to the inductor. A control circuit includes a first current sensor having inputs and an output. The current sensor inputs are coupled to terminals of the inductor, and the current sensor includes tunable time constant circuit coupled between the current sensor inputs and the current sensor output. An average current sense circuit has an input and output, in which the input is coupled to one of power input or the power output. An inner loop gain circuit has an input coupled to the current sensor output. A direct current resistance (DCR) control circuit has first and second DCR inputs and an output. The first DCR input is coupled to the output of the average current sense circuit. The second DCR input is coupled to an output of an outer loop gain circuit. The output of the DCR control circuit is coupled to a gain adjust input of the inner loop gain circuit.

DETAILED DESCRIPTION

Example embodiments relate determining properties of inductors in power converters, such as a switch mode power supplies. For example, a power converter has a power stage that includes switch circuit and an external inductor. Because properties of the inductor used in a given application, including DC resistance (DCR) and inductance, can vary widely from its device specifications, it is desirable to determine such properties to optimize performance of the power converter.

As described herein, a controller of the power converter thus includes a time-constant control circuit and a DCR control circuit. The time-constant control circuit control circuit operates during a calibration phase, such as at start-up (e.g., power up) or reset of the power converter, to determine the time constant of the inductor. The time-constant control circuit is configured to tune a time-constant circuit, such as a resistor-capacitor (RC) circuit, to have a time constant that matches a time constant of the inductor of the power converter. In an example, a current sensor circuit includes the RC circuit, and is coupled to the inductor of the power converter. For example, the time-constant control circuit is configured to tune the RC circuit (e.g., by adjusting the C in the RC circuit) so a zero crossing of a voltage provided by the RC circuit is aligned with a sensed zero crossing of the inductor current.

The DCR control circuit can operate continually or intermittently during normal operation of the power converter to determine the DCR of the inductor. For example, the DCR control circuit is configured to adjust gain of the controller to match the DCR of the inductor. The gain adjustments can be made responsive to a measure of average inductor current and a requested inductor current (e.g., a current command signal). In an example, the current actually delivered to a load, such as a battery, provides an indication of average inductor current.

This approach described herein further can use lower current draw for identification or calibration compared to existing approaches. Additionally, the DCR control circuit can implement continual gain adjustment of the gm for the average current feedback enables constant loop gain in the current feedback, which tends to be largely independent of DCR or variations in DCR due to temperature changes. As a result, the power converter can be implemented in devices and systems in so as to be largely immune to changes in inductor values or parasitic board resistances. The circuits and methods described are further particularly applicable to high power devices, such as may include inductor currents up to 20 A or higher. Such high-power applications often require large inductors having very small inductor DCR (e.g., 1 mΩ to 10 mΩ). Inductors having small DCR further complicates detecting its DCR value using existing approaches, in which a large DC voltage is applied to the inductor.

Figure 1:
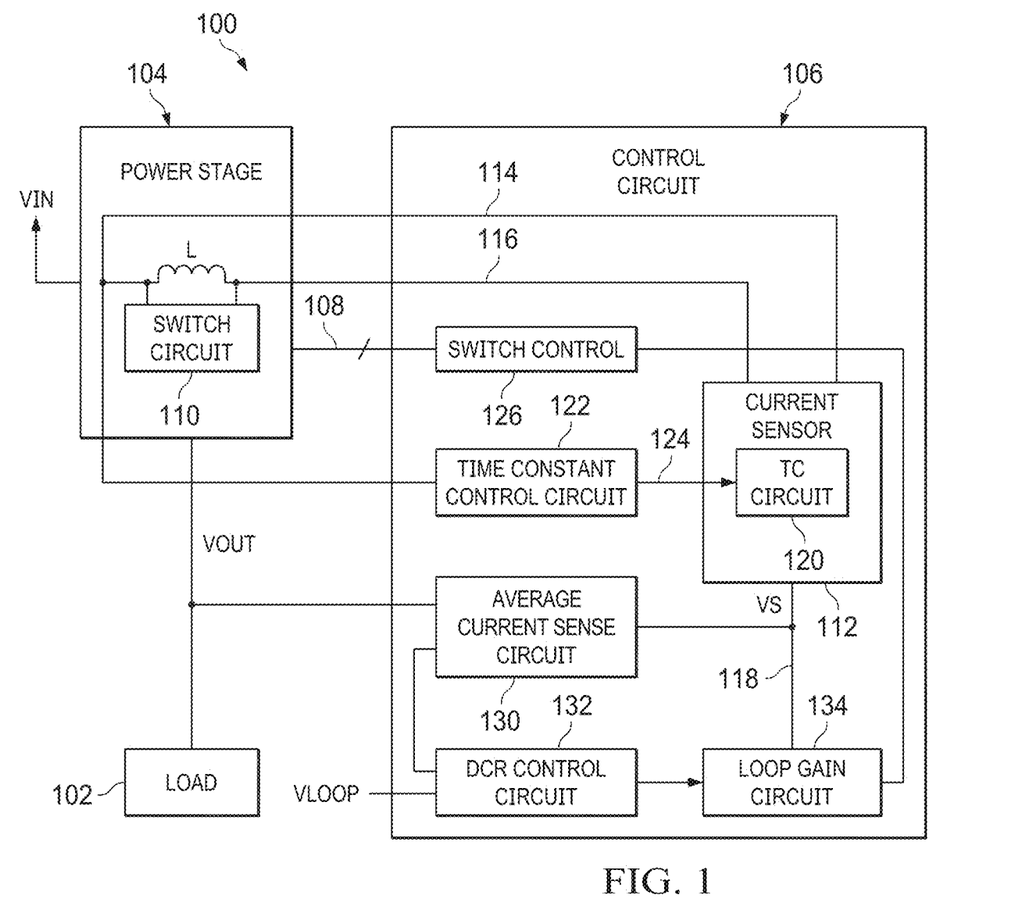
FIG. 1 is a block diagram of an example power converter system.

FIG. 1 is a block diagram of an example power converter 100. For example, the power converter system 100 is configured to supply electrical power to a load 102. In an example, the load 102 includes one or more battery cells and the power converter is a battery charger. Thus, the power converter 100 can be configured to deliver high current to the load. The power converter 100 includes a power stage 104 and a control circuit (e.g., a controller) 106. The power stage 104 has a power input coupled to a voltage source, which is configured to provide an input voltage VIN. The power stage 104 also has an output that is adapted to be coupled to the load 102. The power stage 104 is coupled to the control circuit 106 through one or more electrical connections 108, and the power stage is configured to convert the input voltage VIN to an output voltage VOUT responsive to control signals provided by the control circuit 106. For example, the power stage 104 includes a switch circuit 110 and an inductor L. The switch circuit includes an arrangement of one or more switch devices coupled to terminals of the inductor L. The switch devices of the circuit 110 are configured to control current through the inductor L responsive to the control signals to provide the output voltage VOUT to the load 102. For example, a switch control (e.g., pulse generator and driver circuitry) 126 is configured to provide the control signals to control turning on and off respective switch devices of the switch circuit 110.

The control circuit 106 includes a current sensor 112 having inputs 114 and 116 and an output 118. The current sensor inputs 114 and 116 are coupled to respective terminals of the inductor L. The current sensor 112 also includes a tunable time constant circuit 120, and the current sensor is configured to provide a voltage signal VS at 118 representative of the current through the inductor L.

A time-constant control circuit 122 has inputs coupled to the input 114 of the current sensor and to the output 118 of current sensor 112. The time-constant control circuit 122 also has an output 124 coupled to the time constant circuit 120. The time-constant control circuit 122 is configured to tune the time constant circuit 120 responsive to detecting a zero crossing of the current sensor output 118 and a zero crossing of the signal at 114 representative of inductor current. At power up, the control circuit 106 implements a calibration process to configure the time constant circuit 120. For example, during the calibration, the switch control circuit 126 provides a fixed on-time pulse to activate one or more switch devices coupled at 114, which enables current to increase in the inductor L while with the other side of the inductor at 116 is coupled to an electrical ground (e.g., though another switch device). The switch devices coupled at 114 can be implemented as a field effect transistor having a body diode. During the off-time of the pulse, the diode continues to conduct the inductor current, which decreases at a rate functionally related to the time constant of the inductor L. The voltage VS at 118 tracks the inductor current and varies according to the time-constant of the time constant circuit 120. The time-constant control circuit 122 is configured to tune the time constant circuit 120 to align the zero crossing of VS to match the zero crossing detected at 114, which is representative of the actual inductor current. In an example when the time constant circuit 120 includes an RC circuit having a variable capacitor, the time-constant control circuit 122 is configured to adjust the capacitance to perform the zero crossing alignment of VS with respect to the inductor current. The capacitance value can be set, such as by setting the value of one or more registers.

The control circuit 106 also includes a current sense circuit 130 and a DCR control circuit 132. The current sense circuit 130 can be coupled to the output or input of the power stage 104, and configured to provide a current sense signal representative of an average current through the inductor L. The DCR control circuit 132 has one input coupled to the output of the current sense circuit 130 and another input configured to receive a current command signal, shown as a loop voltage VLOOP. The DCR control circuit 132 has an output coupled to a tunable loop gain circuit 134. For example, the loop gain circuit 134 resides within a feedback loop of the control circuit 106, and is configured to set a loop gain for the loop responsive to a gain adjustment signal provided by the DCR control circuit 132. The DCR control circuit 132 is configured to provide the gain control signal to adjust the gain of the loop gain circuit 134 responsive to the current sense signal and the current command signal. As described herein, the DCR control circuit 132 can operate continuously during normal operation of the power converter 100 (as part of the feedback loop of the power converter control circuit 106). The continual gain adjustments for average current feedback allows for constant loop gain in the current feedback largely independent of DCR or variations in DCR due to temperature changes. As a result, the power converter control circuit 106 can operate largely immune to changes in inductor values or parasitic board impedance. Ultimately, because the system 100 is configured to autonomously determine inductor properties, the user (e.g., customer) does not need to account for the choice of inductor that is used in the power converter.

Figure 2:
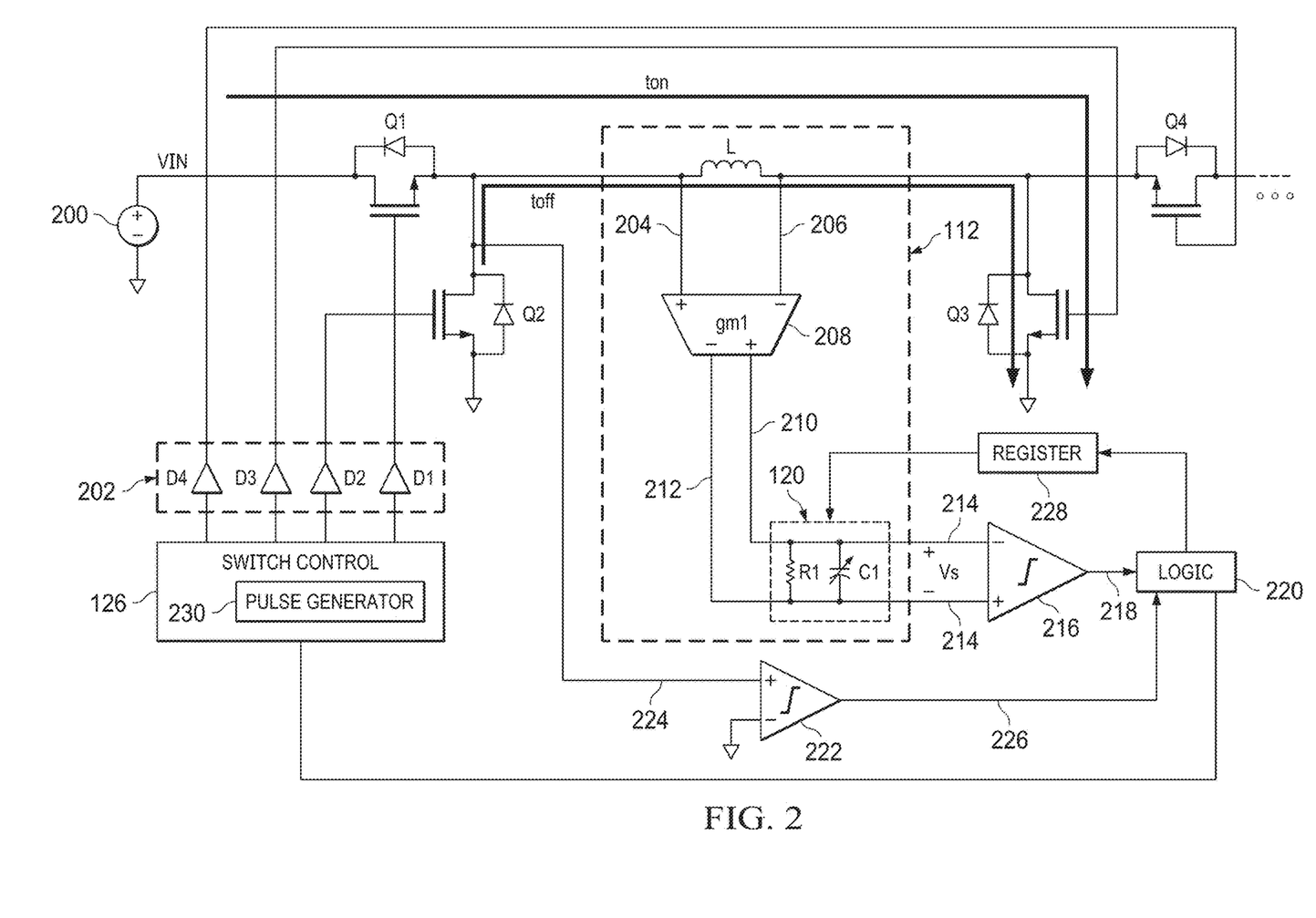
FIG. 2 is a circuit diagram showing an example time constant control circuit.

FIG. 2 is a circuit diagram of part of a power converter showing an example in which the time constant control circuit 122 is coupled to the power stage 104. The power stage 104 includes the inductor L and the switch circuit 110. The particular properties of the inductor L (e.g., time constant and DCR) are unknown. The time constant control circuit 122 can be implemented in the power converter system 100 of FIG. 1. Accordingly, the description of FIG. 2 also refers to FIG. 1. In the example of FIG. 2, the switch circuit 110 includes switch devices shown as power field effect transistors (FETs) Q1, Q2, Q3 and Q4, each having a body diode coupled between its respective source and drain. In one example, the power FETs are NFETs configured as an H-bridge. As shown in FIG. 2, Q1 has a source coupled to the inductor L and a drain coupled to in input voltage source 200. The voltage source 200 is configured to provide a DC input voltage VIN. Q2 has a drain coupled to the source of Q1 and a source coupled to ground. Q3 has a drain coupled to the other terminal of the inductor L and source coupled to ground. The gates of Q1, Q2 and Q3 are coupled to a switch control circuit 126 through drive circuitry 202, which includes respective gate drivers D1, D2, D3 and D4. The switch control circuit 126 is configured to activate and deactivate the respective switch devices Q1, Q2, Q3 and Q4 to control current through the inductor L. The drain of Q4 can be coupled to a load, such as a battery (not shown). In other examples, different numbers and types of switch devices can be configured to supply current to the inductor L according to application requirements.

The time constant control circuit 122 includes the current sensor 112 coupled to terminals of the inductor L. In the example of FIG. 2, the current sensor 112 includes a gain stage 208 having inputs 204 and 206 coupled to the respective terminals of the inductor L. The gain stage has outputs 210 and 212 coupled to the time constant circuit 120. The gain stage 208 is configured to have a gain, shown as gm1, and provides an amplified output across differential outputs 210 and 212 representative of a measured voltage across the inductor L. As described herein, the current sensor 112 is configured to provide an output representative of inductor current responsive to the measured voltage across 204 and 206.

In one example, the time constant circuit 120 is an active circuit, such as an RC filter having a variable capacitor C1 and resistor R1 coupled in parallel to respective outputs 210 and 212 of the differential amplified output. In other examples, different types of active circuits can be used. As described herein, the time constant circuit 120 is used to determine the time constant of the inductor L. The current sensor 112 has an output (e.g., shown as a differential output 214) coupled to an input of a zero crossing detector circuit 216. The zero crossing detector circuit 216 has an output 218 coupled to an input of a logic circuit 220. The current sensor 112 is configured to provide an output signal VS at 214 representative of current through the inductor L. Thus, the measured voltage VS (e.g., representative of current through L) can provide an estimate of the current through the inductor, and the RC filter can be tuned so the sensed current from VS matches actual inductor current. The zero crossing detector 216 is configured to detect zero crossings in the sensed voltage VS at 214 and provide a zero crossing signal at 218 representative of when the inductor current reaches 0 A. For example, the sensed voltage VS at 214 can be represented as follows:

$$Vs = I_L R_{DCR} \frac{gm1 * R_2 \left( s \frac{L}{L_{DCR}} + 1 \right)}{(sR_2 C_1 + 1)}$$

Another zero crossing detector 222 has an input 224 coupled to a high-side terminal of the inductor L to which the input 204 of the current sensor 112 is coupled and to which the drain of Q2 is also coupled. The zero crossing detector 222 has an output 226 coupled to another input of the logic circuit 220. The zero crossing detector 222 is configured to detect zero crossings at 224, which is responsive to inductor current through the body diode of Q2, and provide a zero crossing signal at 226 representative of an instantaneous inductor current. By using the body diode of Q2 to identify the zero crossing of the inductor current, the identification does not require an analog-to-digital converter or other more complicated circuitry. For example, because the diode is conducting and Q2 is off, the voltage changes from about −0.6 V (e.g., one diode drop) to 0 V. Thus, using the diode allows the voltage change to be large, which allows the circuit to be simple in design and effectively detect inductor current is at 0 A.

The logic circuit 220 is configured to detect when the zero crossings occur relative to each other. In one example, the logic is configured to determine when the zero crossings match. The logic circuit 220 has an output coupled to an input of a register circuit 228. The register circuit 228 has an output coupled to the time constant circuit 120. For example, the logic circuit 220 is configured to set a value of the register 228, which is used to tune a capacitance value of the capacitor C1. The value of C1 configures the time constant of the time constant circuit 120. As described herein, when the logic circuit 220 detects a match between zero crossings at 218 and 226 is representative of the time constant (e.g., R*C) of the time constant circuit 120 matches the time constant (e.g., L/DCR) of the inductor. As described herein, after the time constant circuit 120 is tuned, DCR control circuit is configured to perform continuing (e.g., always running) adjustments for DCR of the inductor.

The switch control circuit 126 is configured to operate the power converter in a calibration phase, such as can be implemented to determine the time constant of the inductor at power up or reset of the power converter. The switch control circuit 126 includes a pulse generator 230 configured to supply control pulses having a duty cycle. In an example, the pulse generator 230 includes a pulse width modulation (PWM) generator configured to provide the signal control pulses responsive to a ramp signal and a reference signal. During the calibration phase, the switch control circuit 126 controls the pulse generator 230 to supply the pulses to the gates of Q1 and Q3 with a fixed on time while Q2 and Q4 are held off. This allows inductor current to increase during the on time while Q1 and Q3 are both on, shown as current path ton. When the switch control circuit 126 turns off Q1 and keeps Q3 on, while Q2 and Q4 remain off, inductor current is pulled through the diode of Q2, through inductor L and through Q3, shown as current path toff. The inductor current during the off interval (toff) decreases at a rate functionally related to the time constant of the inductor L until the diode of Q2 ceases conduction and turns off. During such calibration, the zero crossing detected at 224 is representative of when the current through the diode of Q2 ceases conduction. The logic circuit 220 is configured to control the value of the register to tune the time constant of the circuit 120 so that VS measured at 214 and the inductor current measured at 224 have simultaneous zero crossings. In one example, the logic is configured to increment the register value by a counter value (e.g., from a minimum to a maximum value or from a maximum to a minimum value). In another example, the logic is configured to implement a binary search for tuning the time constant circuit to achieve a match in zero crossings.

Figure 3:
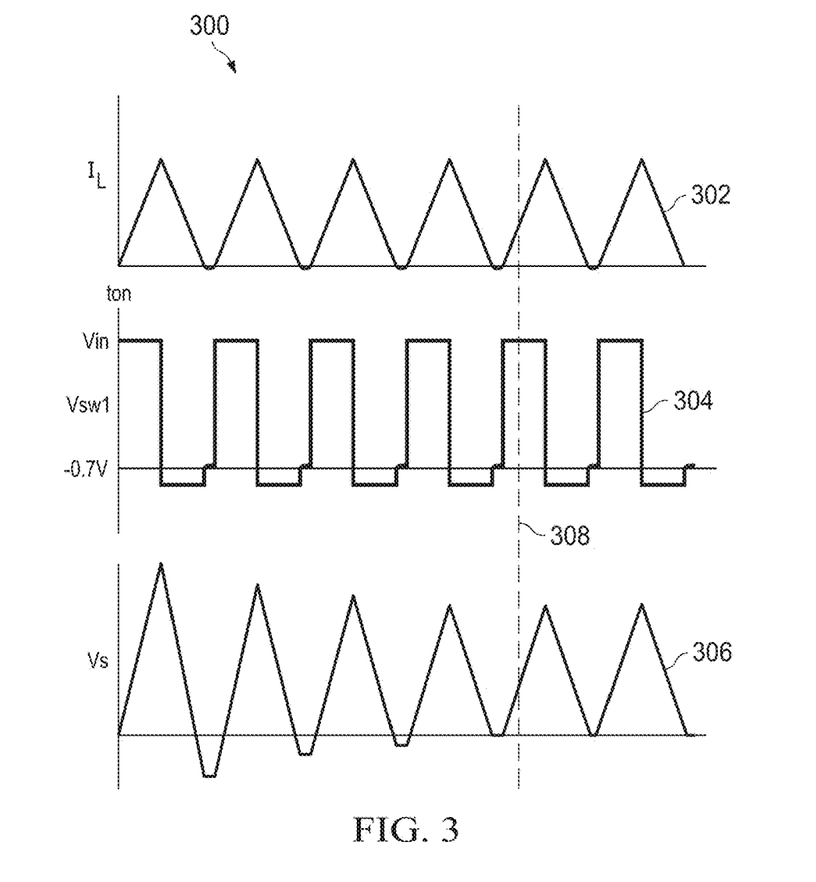
FIG. 3 is a signal diagram showing examples of signals in the circuit of FIG. 2.

As a further example, FIG. 3 is a signal diagram 300 showing examples of signals in the circuit of FIG. 2 during time constant calibration of the power converter 100. The signal diagram 300 includes a plot 302 of current through the inductor L, a plot 304 of the voltage at 224, and a plot 306 of the voltage VS measured at 214. Thus, when Q1 and Q3 are turned on for a fixed time interval, the inductor current IL builds until Q1 is turned off. When Q1 is turned off, the inductor current flows through the diode of Q2 and decreases accordingly. During the off time interval, the voltage at the drain of Q2, as shown at 304, is at one negative diode drop below 0 V, while the diode conducts the decreasing inductor current. The voltage VS decreases at a rate responsive to the capacitance value to which the logic circuit 220 has tuned the capacitor C1 during the current time period of the pulse signal. A different value thus can be used for each pulse time period during calibration until the logic circuit 220 detects a match in the zero crossings occurs between VS (shown at 306) and IL (shown by 304). The match at zero crossings is shown at 308 in FIG. 3. The value of capacitance for C1 that achieves the zero crossing match 308 can be stored in the register 228 to use during operation of the power converter 100. The tuned time constant value can remain fixed during such operation or the calibration process can be repeated to reconfigure the time constant circuit 120. The current sensor 112 can be implemented as part of a current feedback loop of the control circuit 106.

Figure 4:
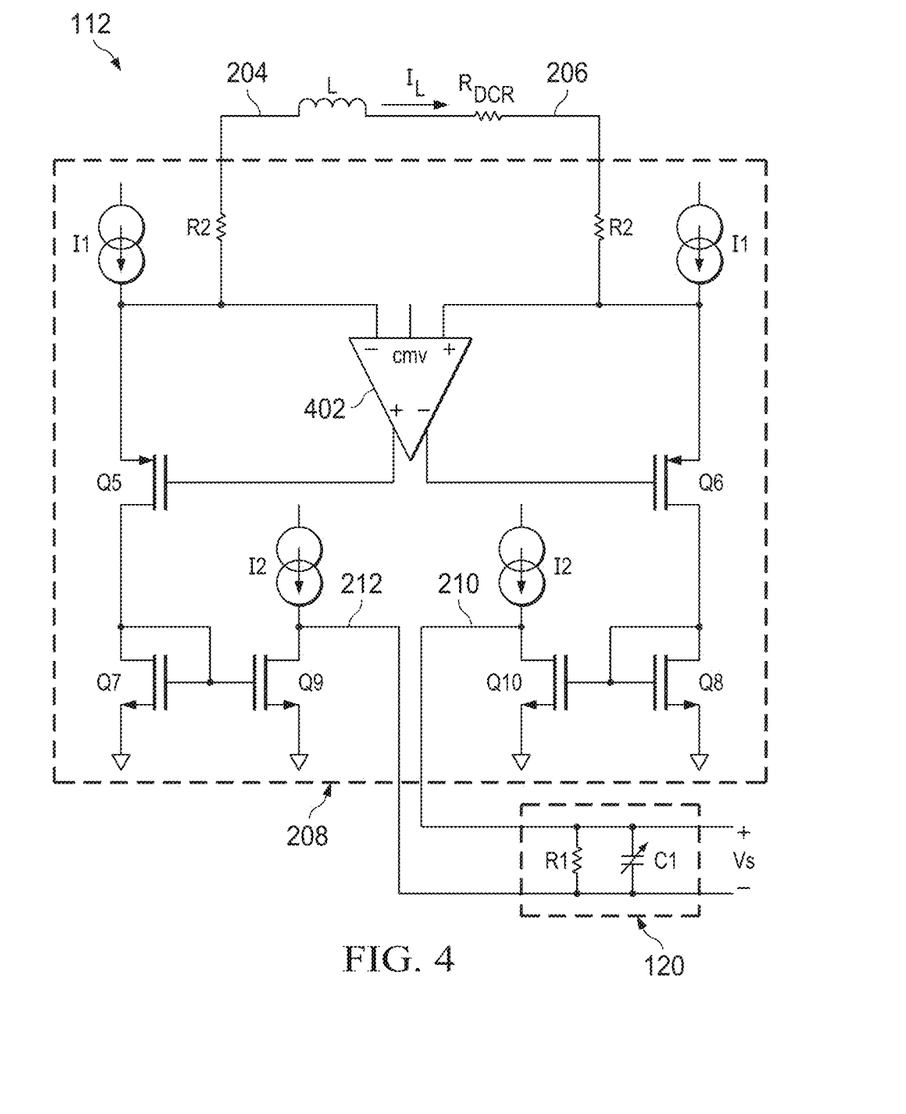
FIG. 4 is a circuit diagram showing an example current sensor circuit that can be used in the power converter system.
Figure 5:
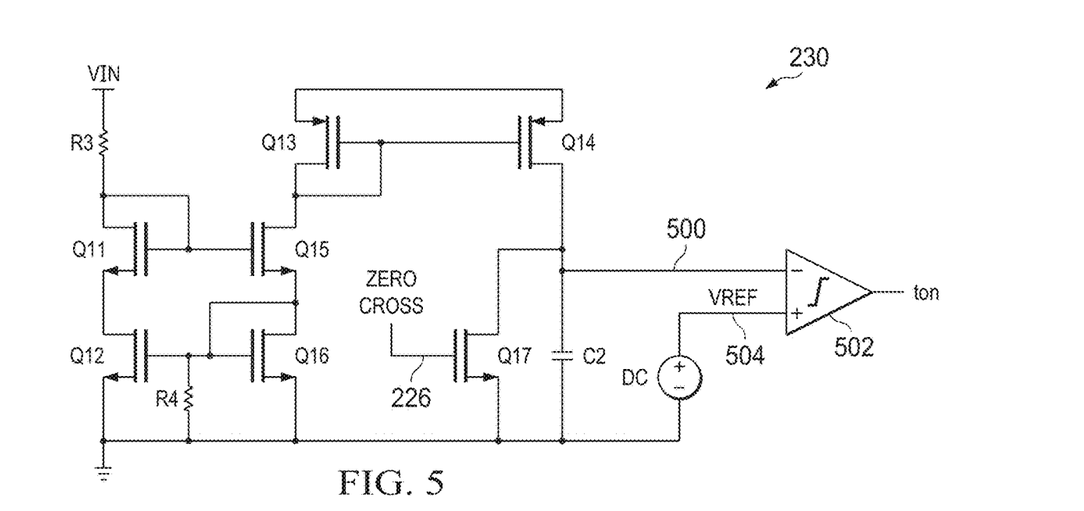
FIG. 5 is a circuit diagram showing an example pulse generator that can be used in the time constant control circuit of FIG. 2.

As an example, FIG. 4 is a circuit diagram showing an example current sensor 112 that can be used in the power converter system. The current sensor circuit includes a differential amplifier 402 having a differential input 404 coupled to inputs 204 and 206 through respective matched resistors R2. Each of the resistors R2 is coupled to an inductor terminals. The inputs 204 and 206 can be configured as low impedance inputs to allow the gain of amplifier 402 to be set by R2. Current sources are coupled to each respective differential input 404 and to sources of transistors, and are configured to supply current I1. Current mirror transistors Q7 and Q8 (e.g., PFETs) are configured to mirror the current I1 to respective output transistors Q9 and Q10 (e.g., NFETs). The outputs 212 of the sensor 112 are coupled to drains of Q9 and Q10. As described above, the time constant circuit 120, which includes R1 and C1, is coupled to the outputs 210 and 212. The time constant circuit 120 is configured to provide VS, which is representative of inductor current. In the example of FIG. 5, the current sensor 112 is a differential configuration, which is chopped to remove offsets. In the example of FIG. 4, the output voltage VS can be expressed as follows:

$$Vs = I_L R_{DCR} \frac{R_2\left(s\frac{L}{R_{DCR}} + 1\right)}{R_1(sR_2C_1 + 1)}$$

From the above expression, when the time constant of the time constant circuit 120 equals the time constant of the inductor L, the above equation reduces to VS=IL*RDCR.

The resistors R1 and R2 can be configured to track each other so as to help stabilize the gain of the current sensor 112.

FIG. 5 is a circuit diagram showing an example pulse generator 230 that can be used in the time constant control circuit 122 of FIG. 2. Accordingly, the description of FIG. 5 also refers to FIG. 2. Other configurations of pulse generators can be used to provide pulses for use in determining the time constant of the inductor L during the calibration phase. In the example of FIG. 5, the pulse generator 230 is configured to provide the pulse at an output 502 as a voltage pulse having a fixed on time, shown as ton, which is proportional to VIN and responsive to the zero crossing signal provided at 226 by zero crossing detector 222

For example, a transistor (e.g., NFET) Q11 is coupled to the input voltage VIN through a resistor R3. The source of Q11 is coupled to drain of another transistor (NFET) Q12. Q11 is configured as a diode-connected transistor and has its gate coupled to the gate of transistor (e.g., NFET) Q15, and the source of Q15 is coupled to the drain of another diode-connected transistor Q16. The gate of Q16 is coupled to the gate of Q12, and a resistor is coupled between the gate and ground. A current mirror of transistors Q13 and Q14 is coupled between the drain of Q15 and an input 500 of a comparator 502. A capacitor is coupled between the input 500 and ground in parallel with a transistor (e.g., an NFET) Q17. A DC reference voltage source is coupled to the other input 504 of the comparator 502, and is configured to supply a reference voltage VREF to such input 504. The input at 500 across the capacitor thus generates an increasing ramp signal by charging the capacitor C2 responsive to the input voltage and reset to 0 V by the detected zero crossings (provided by zero crossing detector 222) at 226. The comparator 502 thus triggers the pulse with the constant on time TON responsive to the increasing voltage at 500 relative to the DC voltage VREF. In the example of FIG. 5, the on time of the TON pulse is expressed as follows:

$$TON = \frac{C2 * VREF}{ICHG} = \frac{C2 * VREF * R3}{VIN}, \text{ where } ICHG = \frac{VIN}{R3}$$

Figure 6:
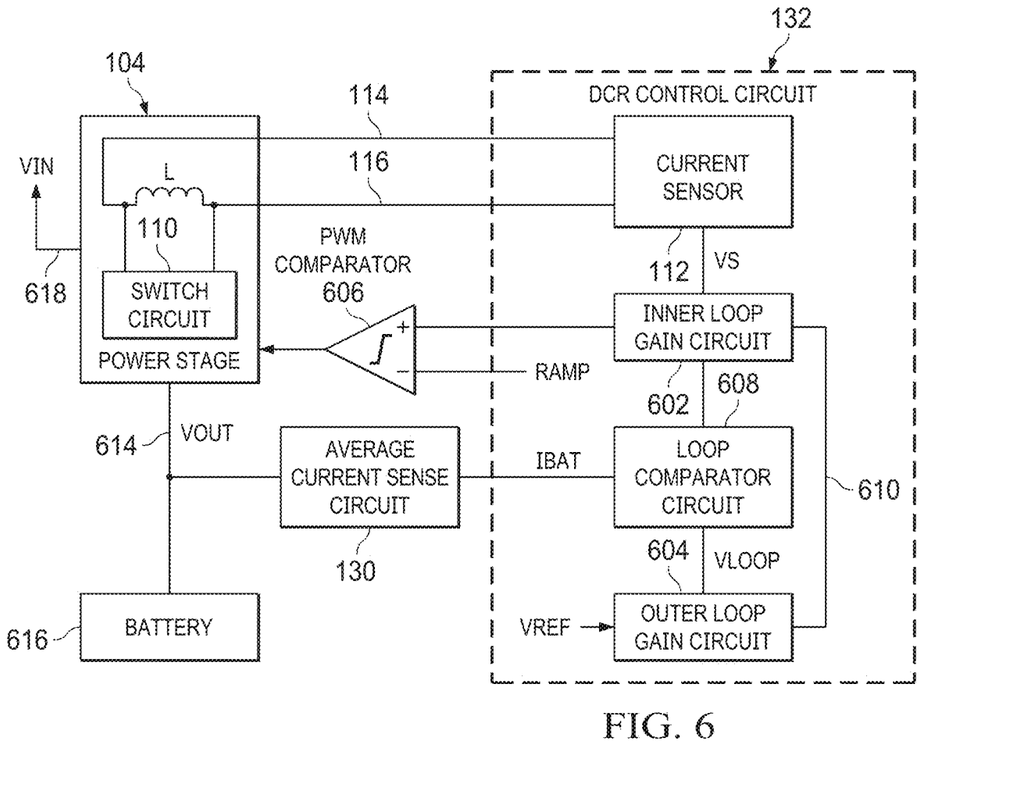
FIG. 6 is a block diagram of part of a power converter showing an example DCR control circuit.

FIG. 6 is a block diagram of part of a power converter showing an example DCR control circuit 132. The time DCR control circuit 132 can be implemented in the power converter system 100 of FIG. 1. Accordingly, the description of FIG. 6 also refers to FIG. 1. The DCR control circuit 132 is configured to determine the DCR of the inductor L and adjust the gain of the control loop responsive to the DCR. In an example, the DCR control circuit 132 is configured to adjust the gain of current feedback responsive to changes in the DCR that can occur during operation. Such gain adjustments can be implemented to compensate for variations in DCR, including responsive to temperature or other operating parameters that can change over time.

In the example of FIG. 6, DCR control circuit 132 has an inner loop gain circuit 602 and an outer loop gain circuit 604. The inner loop gain circuit 602 includes the current sensor 112, which is coupled to terminals of the inductor L of the power stage 104. As described herein, the current sensor 112 includes a time constant circuit configured to set a time constant for the inner loop gain circuit 602. The current sensor 112 thus is configured to provide a feedback signal representative of sensed inductor current, shown as the voltage VS. The inner loop gain circuit 602 has an output coupled to an input of a PWM comparator 606. The inner loop gain circuit 602 also includes inputs coupled to respective outputs of a loop comparator circuit 608 and the outer loop gain circuit 604. The inner loop gain circuit 602 is also configured to implement a gain (gm2) responsive to signals received at its inputs.

The outer loop gain circuit 604 has an input configured to receive a reference voltage signal VREF, which is representative of desired converter regulation operating parameters. The outer loop gain circuit 604 has an output coupled to an input of the loop comparator circuit 608. The outer loop gain circuit 604 is configured to provide the input a loop current command signal VLOOP having a value specifying a desired current command for the inductor current. The outer loop gain circuit 604, which has a gain (gm3) set responsive to VLOOP, is configured to set the reference for the inner loop. The outer loop gain circuit 604 also has an output coupled to another input of the inner loop gain circuit 602. For example, the outer loop gain circuit 604 is configured to provide an output signal (e.g., a voltage), shown at 610, to the inner loop vain circuit 602 responsive to VLOOP and according to gain gm3. The value of VLOOP can vary during operation and power requirements of the power converter. Thus, the value of the output at 610 likewise can vary during operation responsive to changes in VLOOP.

As described above, the loop comparator 608 has a first input configured to receive VLOOP from the outer loop gain circuit 604. The loop comparator 608 also has a second input coupled to an output of an average current sense circuit 130. In the example, of FIG. 6, the average current sense circuit 130 is coupled to an output 614 of the power converter 100. In other examples, the current sense circuit 130 is coupled to an input 618 (see, e.g., FIG. 9). In the example of FIG. 6, a battery 616 is coupled to the output 614. For example, the power converter 100 is implemented as battery charger configured to charge one or more cells of the battery 616, which is coupled to the output 614. Other types of loads can be coupled to the output 614 of the power converter 100. The average current sense circuit 130 is configured to provide an output signal IBAT responsive to the current supplied to the battery 616 (or other load coupled at the output). The output signal IBAT has a value that has a known relationship with respect to the inductor current, which can vary depending on the mode of the power converter 100. For example, in a buck mode, the desired inductor current (e.g., as specified by VLOOP) should be equal to the battery current IBAT. In the example if a boost mode power converter, the desired inductor current (e.g., as specified by VLOOP) should be (1−D)*IBAT.

The loop comparator 608 is configured to provide a gain adjust signal to the inner loop gain circuit responsive to VLOOP and IBAT. The inner loop gain circuit 602 thus is configured to implement gain adjustments responsive to the gain adjust signal. The inner loop gain circuit 602 is further configured to provide an output current command signal (e.g., a voltage) to the input of the PWM comparator 606 responsive to the gain adjust signal and the output 610 provided by the outer loop gain circuit 604. As a further example, in steady state operation, it can be shown that the sensed voltage across the inductor L (VS) can be expressed as follows:

$Vs = IL*R_{DCR}$, which can be rewritten as $gm2*\overline{IL}*R_{DCR} = gm3*VLOOP$, where $\overline{IL}$ is the average inductor current, and gm2 and gm3 are representative of gains of the respective inner and outer loop gain circuits 602 and 604.

Solving for VLOOP, the above equation can further be rewritten as:

$$VLOOP = \frac{gm2}{gm3} * \overline{IL} * R_{DCR}$$

Thus, the loop comparator 608 is configured to provide the gain adjust signal to continually adjust the gain gm2 of the inner loop gain circuit 602 to match the actual battery current to the desired current. In an additional or alternative example, the loop comparator 608 could be configured to provide the gain adjust signal to continually adjust the gain gm3 of the outer loop gain circuit 604. As a result, the DCR control circuit 132 is configured to determine a value of DCR and to thereby compensate for differences in the DCR of the inductor ($R_{DCR}$). This form of compensation, which can be performed during operation, is referred to herein as adaptive DCR optimization.

Figure 7:
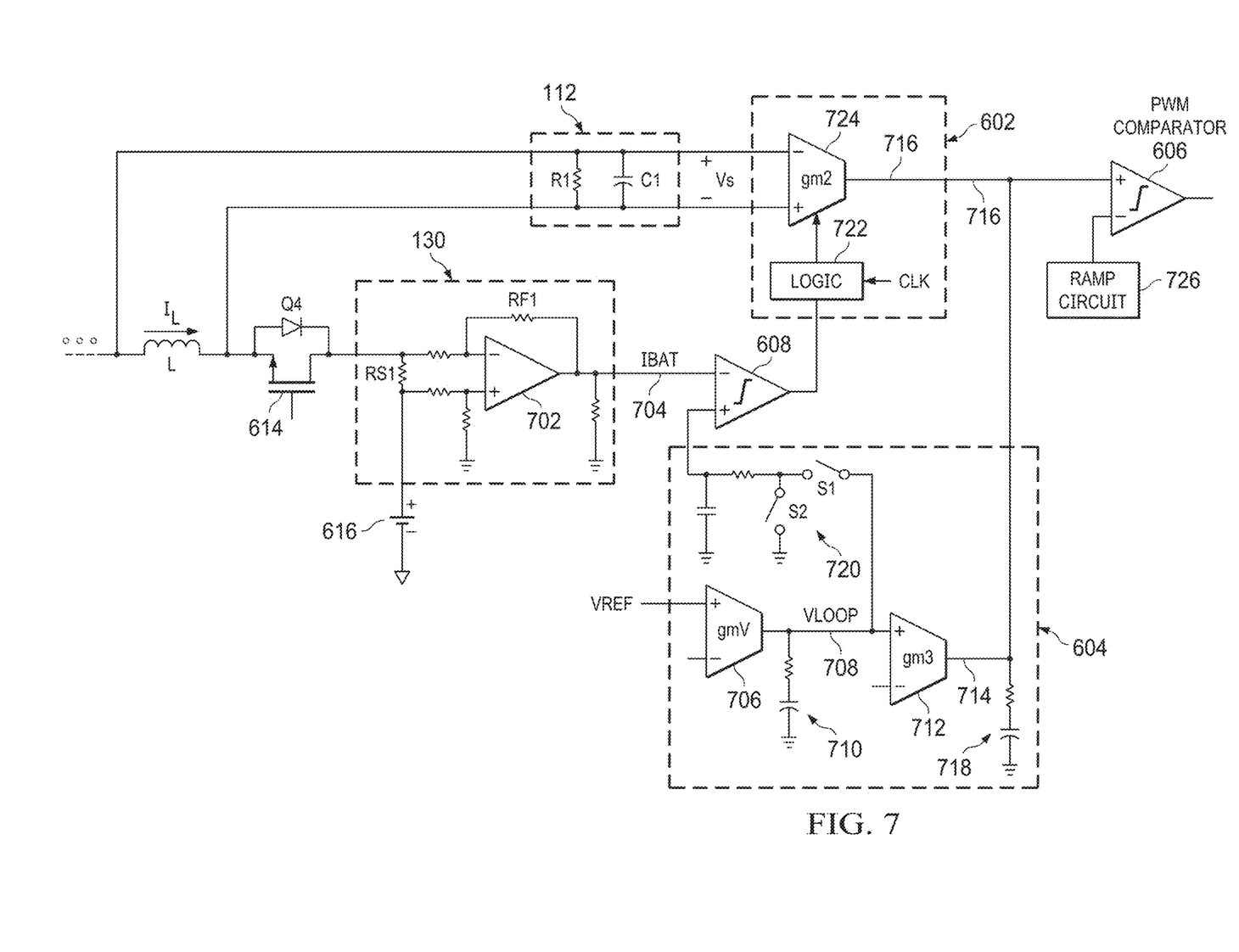
FIG. 7 is a circuit diagram showing an example DCR control circuit.

FIG. 7 is a circuit diagram showing an example embodiment of the DCR control circuit 132 shown in FIGS. 1 and 6. Accordingly, the description of FIG. 7 also refers to FIGS. 1 and 6. As shown in FIG. 7, current sense circuit 130 is coupled to the output of the power converter 100. For example, the current sense circuit 130 includes sense resistor RS1 (e.g., RS1≈5 mΩ) coupled between the drain of Q4 and an input of the battery 616. Respective terminals of RS1 are coupled to inputs of a difference circuit 702 through respective resistors. Difference circuit 702 includes a feedback resistor RF1 coupled between an output 704 of the difference circuit and its inverting input. Difference circuit 702 is configured to provide an output signal IBAT at 704, such as a voltage responsive to the voltage potential across RS1 having a value representative of the current supplied to the battery 616 (or other load that may be coupled to the output). In the example of FIG. 7, the output 704 is coupled to an inverting input of comparator 608. The non-inverting input of comparator 608 is coupled to an output of the outer loop gain circuit 604. For example, the outer loop gain circuit 604 is configured to provide a signal to the non-inverting input of comparator 608, in which the signal is representative of an average desired inductor current responsive to VLOOP.

The outer loop gain circuit 604 includes a gain stage 706 having an input coupled to a reference voltage, which may be set by a user (e.g., by setting a digital value in a register and/or using an external resistor). The regulation point further can be set depending on the type of regulation mode (e.g., input current mode, output current mode, input voltage mode or output voltage mode). A filter 710 is coupled at the output 708, such as an RC filter. The gain stage 706 is configured to provide VLOOP at an output 708 responsive to the input VREF. The output 708 is also coupled to an input of another gain stage 712, shown as having a gain gm3. An output 714 of gain stage 712 is coupled to an output 716 of the inner loop gain circuit 602. Another filter 718 is coupled at the output 714, such as an RC filter.

The output 708 is also coupled to the non-inverting input of comparator 608. In the example of FIG. 7, a switch circuit 720 is coupled between the output 708 and the non-inverting input of comparator 608. The switch circuit 720 can include a first switch S1 coupled in series with a resistor, and a second switch S2 coupled between the resistor on the opposite side of the capacitor and ground. The first and second switches S1 and S2 can be controlled mutually exclusively between on and off states (e.g., by logic not shown) depending the mode of the converter and duty cycle.

In an example, the switches S1 and S2 are controlled by the boost mode control signals, which are the same signals that control Q4 and Q3, respectively (see FIG. 2). For example, S1 is when Q4 is on, and S2 is on when Q3 is on. This results in an input to the comparator that is VLOOP*(1−D), which accounts for the inductor current being higher than the output current when operating in boost mode, Thus, the switch circuit is configured to provide a filtered, duty-cycle modulated version of VLOOP to the non-inverting input of the comparator 608. The comparator 608 has an output coupled to an input of a logic circuit 722 of the inner gain loop circuit 602. The comparator 608 is configured to compare IBAT and VLOOP signals and provide an output signal indicative of whether the loop gain is too high or too low responsive to IBAT and VLOOP signals.

The inner gain loop circuit 602 also includes a gain stage 724 having a control input coupled to an output of the logic circuit 722. The logic circuit 722 is configured to generate a gain adjust signal to tune a gain (gm2) of the gain stage 724. In an example, the logic circuit 722 is implemented as a counter to increment or decrement a count value responsive to the comparator output and a clock signal (CLK), in which the count value specifies a gain value. The gain stage 724 is configured to apply a variable gain (gm2) with respect to the input signal VS that is adjusted responsive to the gain adjust signal (e.g., a digital value) provided by the logic circuit 722. In one example, the gain stage 724 can include an arrangement of resistor segments and switches that are coupled respectively into and out of the gain stage 724 responsive to the gain adjust signal. In other examples, different configurations of variable gain stage can be implemented for gain stage 724. The gain stage 724 thus is configured to implement its variable gain and provide an output signal (e.g., a voltage) to a non-inverting input of the PWM comparator 606 responsive to VS and the gain adjust signal. A ramp generator circuit 726 has an output coupled to the inverting input of the PWM comparator 606. The PWM comparator 606 is configured to provide pulses (e.g., through gate drivers D1, D2, D3, D4—not shown in FIG. 7) to control respective switches Q1, Q2, Q3 and Q4 of switch circuit 110 for supplying current to the inductor.

Figure 8:
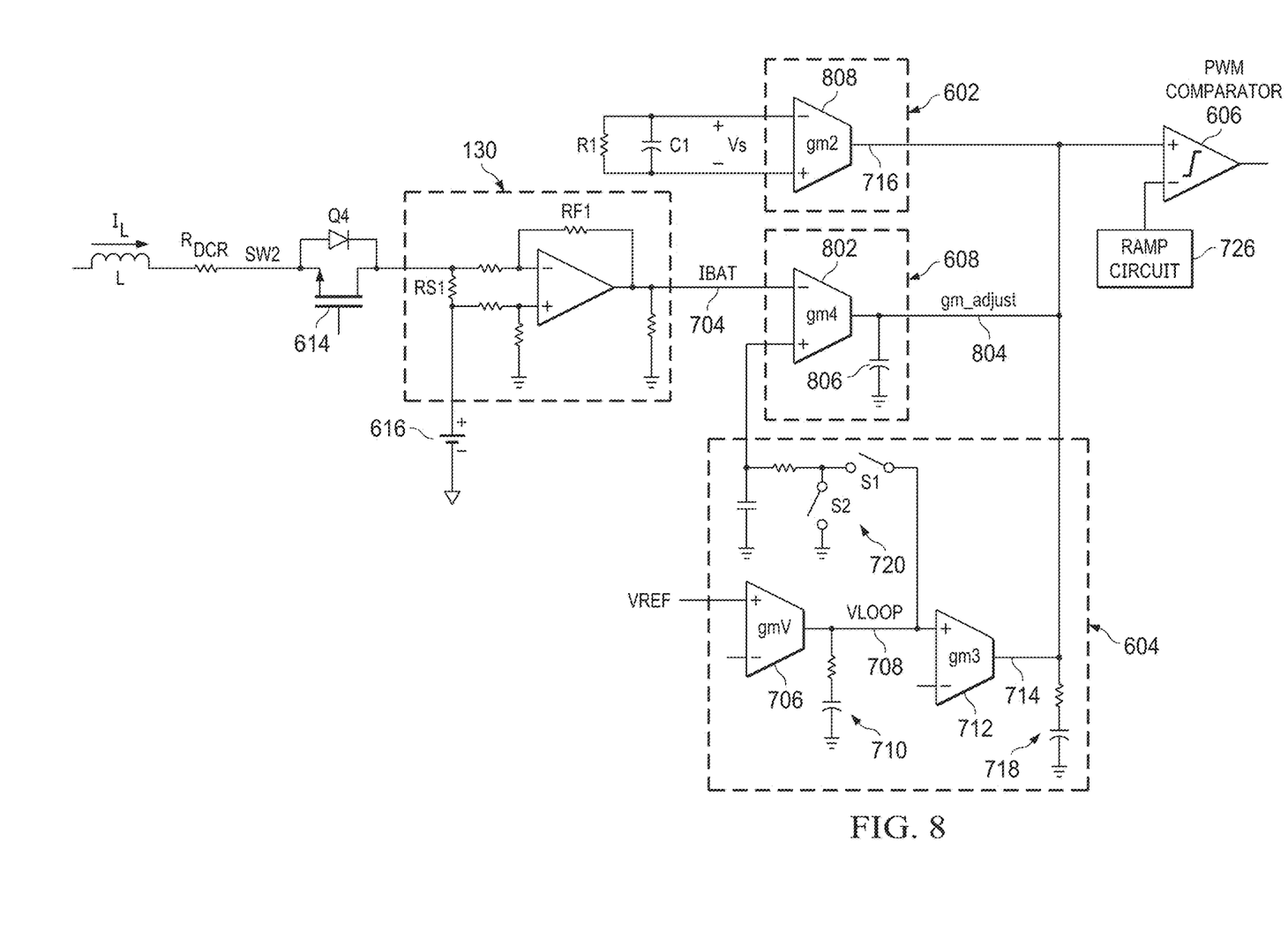
FIG. 8 is a circuit diagram showing another example DCR control circuit.

FIG. 8 is a circuit diagram showing another example embodiment of the DCR control circuit 132 shown in FIGS. 1 and 6. Also, several components of the circuit of FIG. 8 are the same as shown in FIG. 7. Accordingly, the description of FIG. 8 also refers to FIGS. 1, 6 and 7. As shown in FIG. 8, current sense circuit 130 is coupled to the output of the power converter 100. For example, the current sense circuit 130 can be implemented as shown in FIG. 7, and thus configured to provide an output signal IBAT at an output 704. IBAT can be a voltage responsive to the voltage potential across RS1 having a value representative of the current supplied to the battery 616. The output 704 is coupled to an input of the comparator circuit 608.

In the example of FIG. 8, the comparator circuit 608 includes a gain stage 802 having shown as having a gain (gm4). The gain stage 802 has an inverting input coupled to the output 704 of the current sense circuit 130. The non-inverting input of the gain stage 802 is coupled to the output of the outer loop gain circuit 604. For example, the outer loop gain circuit 604 is configured to provide a signal to the non-inverting input that is representative of an average inductor current responsive to VLOOP. The gain stage 802 has an output 804, and a filter 806 can be coupled to the output. For example, the filter can be a RC filter configured to reduce high-frequency components at the output 804. The output 804 is coupled to the output 716 of the inner loop gain circuit 602. In the example of FIG. 8, the inner loop gain circuit 602 includes a gain stage 808, and the outer loop gain circuit 604 is the same as shown in FIG. 7. In contrast to the example of FIG. 7, the gain stage 808 can have a fixed gain gm2. The gain stage 802 is configured to apply a gain adjust signal to the output 716 responsive to IBAT and VLOOP to compensate for differences between VLOOP and IBAT.

The gain stage 724 is configured to apply a gain (gm2) with respect to the input signal VS and provide an output signal at the output 716, which is adjusted responsive to the gain adjust signal (e.g., an analog voltage signal) provided by the gain stage 802. The resulting gain-adjusted signal (e.g., a voltage) is supplied to the non-inverting input of the PWM comparator 606 responsive to VS, the voltage at 714 and the gain adjust signal at 804. Ramp generator circuit 726 has an output coupled to the inverting input of the PWM comparator 606. The PWM comparator 606 is configured to provide pulses (e.g., through gate drivers D1, D2, D3, D4—not shown in FIG. 8) to control respective switches Q1, Q2, Q3 and Q4 of switch circuit 110 for supplying current to the inductor.

Figure 9:
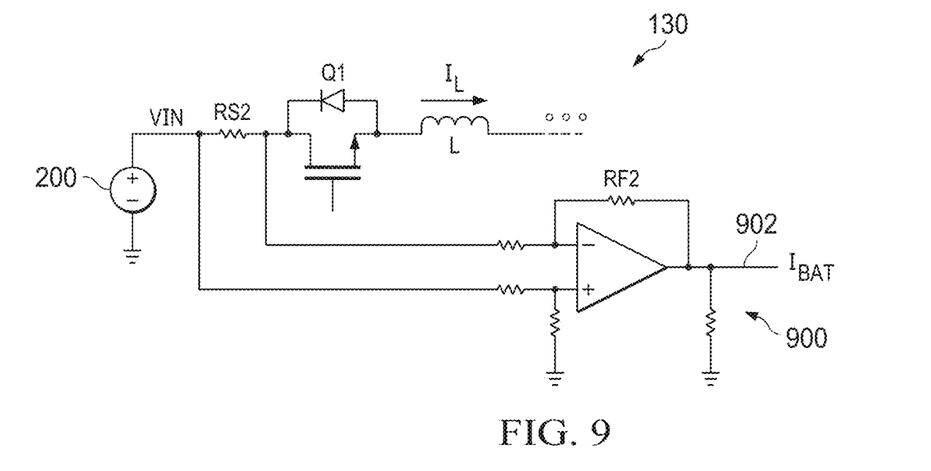
FIG. 9 is a circuit diagram showing an example current sensor that can be used in the DCR control circuits of FIGS. 7 and 8.

FIG. 9 is a circuit diagram showing an example current sense circuit 130 that can be used in the DCR control circuits of FIGS. 1, 6, 7 and 8. The current sense circuit 130 includes sense resistor RS2 (e.g., RS2≈5 mΩ) coupled between the drain of Q1 and an output of the voltage source, which supplies VIN to the power converter 100. Respective terminals of RS2 are coupled to inputs of a difference circuit 900 through respective resistors. Difference circuit 900 includes a feedback resistor RF2 coupled between an output 902 of the difference circuit 900 and its inverting input. Difference circuit 702 thus is configured to provide an output signal IBAT at 704, such as a voltage responsive to the voltage potential across RS2. As described herein, IBAT has a value representative of average inductor current, which is supplied to a load (e.g., battery) coupled to the output of the power converter. In contrast to the examples of FIGS. 1, 6, 7 and 8, the current sense circuit shown in FIG. 9 measures the inductor current at the input instead of the output. Thus, each of the examples herein can measure inductor current either at the input or the output.

Figure 10:
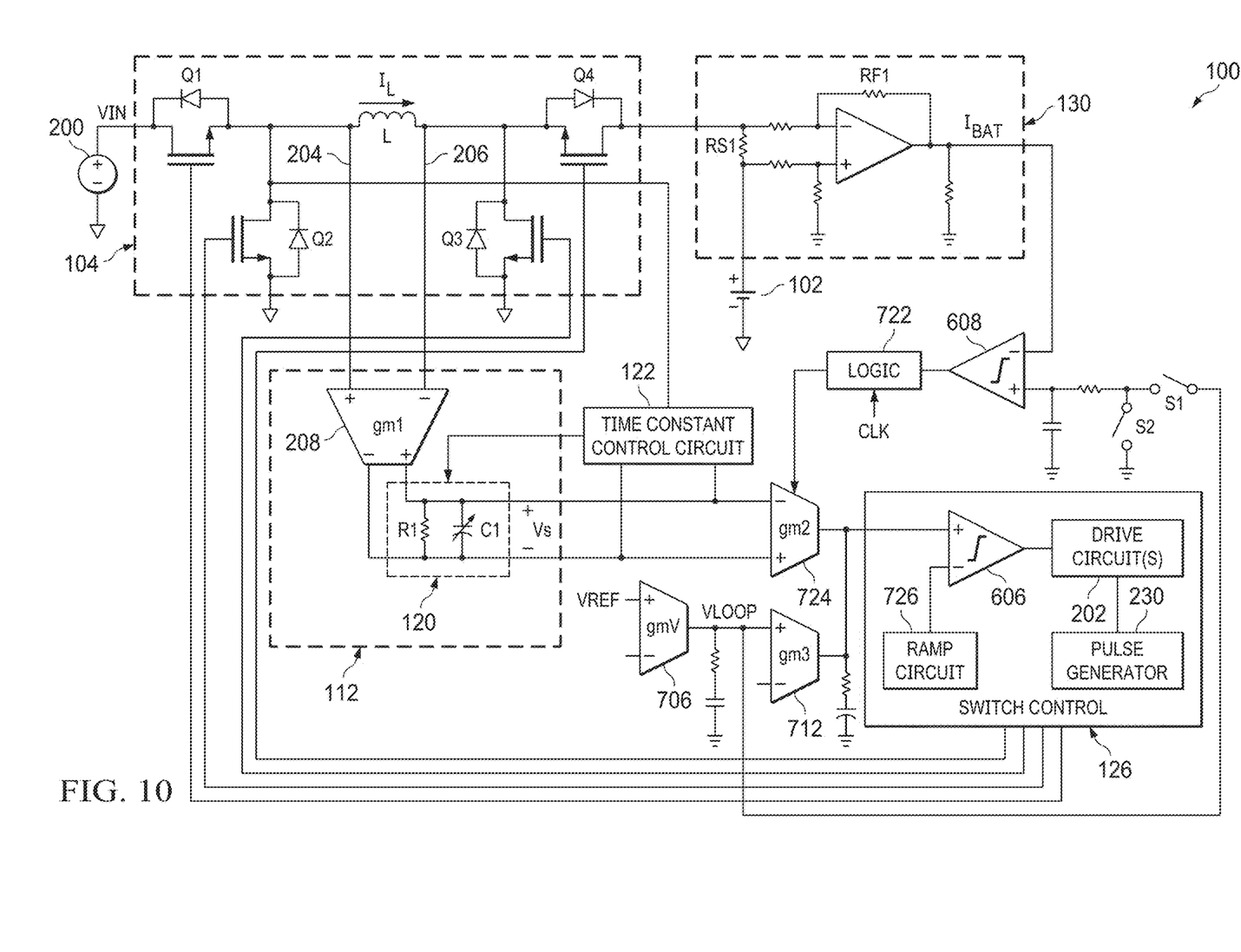
FIG. 10 is a circuit diagram showing an example power converter system.

FIG. 10 is a circuit diagram showing an example embodiment of a power converter system 100. The example of FIG. 10 generally shows an example in which the power converter 100 includes the time constant control circuit 122 of FIG. 2 and the DCR control circuit 132 of FIG. 7. In other examples, the power converter system 100 further may be modified according to any of the example configurations shown and described herein, such as shown in FIGS. 2, 4, 5, 6, 7, 8 and 9. Further variations are also possible based on this description.

As shown, the power converter system 100 includes a power stage 104, which includes the inductor L and the switch circuit 110. The switch circuit 110 includes an arrangement of NFETs Q1, Q2, Q3 and Q4, each having a body diode coupled between its respective source and drain. In the example of FIG. 10, the drain of Q1 is an input of the power converter and is coupled to voltage source 200 configured to provide an input voltage VIN. Current sensor 112 has inputs coupled to terminals of the inductor L, and is configured to provide an output signal, shown as VS, which is representative of inductor current IL.

The power converter 100 also includes time constant control circuit 122 and DCR control circuit 132. As described herein, the circuits 122 and 132 are configured to determine respective inductor properties and to tune one or more respective feedback loops responsive to the determined inductor properties. In an example, the time constant control circuit 122 is enabled (e.g., by a system state machine) to activate during a calibration phase (e.g., at power up). When enabled, the time constant control circuit 122 is configured to tune a time constant circuit 120 (e.g., an RC filter having a variable capacitor C1) to match the time constant of the inductor L. For example, the time constant control circuit 122 can be configured to implement such tuning by matching the zero crossing of VS to the zero crossing of the inductor current (e.g., as detected across the body diode of Q2). In one example, the time constant control circuit 122 is configured to perform such tuning by adjusting the capacitance value of C1 and setting the value of C1 responsive to detecting when the zero crossings match. After the zero crossing match condition has been detected and the value of C1 is tuned to maintain the match condition, the respective tuned value of C1 can remain fixed during operation of the power converter 100. Alternatively, the time constant control circuit 122 may be re-activated to determine the inductor time constant, such as responsive to a reset or other condition in which it would be desirable to recalibrate the time constant circuit 120.

The DCR control circuit 132 is configured to determine the DCR of the inductor L and to adjust the gain of an internal feedback current loop to match the determined DCR. As described, the DCR control circuit 132 is configured according to the example embodiment shown in FIG. 7. For example, a loop comparator 608 has inputs coupled to an output of an average current sense circuit 130 and to an outer loop gain circuit 604. The average current sense circuit 130 is coupled to an output of the converter (e.g., drain of Q1) and is configured to measure current supplied to a load 102, shown as a battery. The comparator 608 thus is configured to receive IBAT, which can be a voltage value representative of the average inductor current, at the inverting input of the comparator. The non-inverting input of the comparator 608 is configured to receive a signal responsive to VLOOP, which is representative of desired inductor current. The comparator 608 is configured to compare IBAT and a filtered VLOOP and provide a comparator output signal to logic circuit 722. The logic circuit 722 is configured to generate a gain adjust signal and adjust the gain of gain stage 724 responsive to the comparator output. The gain adjustments can be implemented continually, such as every clock cycle responsive to IBAT and VLOOP. The period of the clock cycle can be set (e.g., responsive to a register value) to configure the frequency in which the gain is adjusted to compensate for changes in DCR of the inductor.

The gain stage 724 is configured to provide a gain adjusted version of VS to a PWM comparator 606, which is part of switch control circuit 126. The switch control circuit 126 also includes ramp generator circuit 726, pulse generator 230 and drive circuitry 202. The ramp generator circuit 726 has an output coupled to the inverting input of the PWM comparator 606. The PWM comparator 606 is configured to provide pulses to a drive circuit (e.g., including drivers D1, D2, D3, D4—not shown in FIG. 7) to control respective switches Q1, Q2, Q3 and Q4 of switch circuit for supplying current to the inductor L. By tuning the time constant circuit 120 and adjusting gain to match respective inductor properties, as described herein, the power converter is configured to adjust the loop dynamics for changes in the DCR, such as may occur due to temperature and aging. The approach described herein for determining inductor properties can be used for various types of power converters, such as a buck, boost, buck-boost or other converter type, which can vary according to application requirements.

In many applications, the inductor properties can range an order of magnitude or more, such that knowledge of the inductor properties are needed to enable effective and efficient operation of the power converter. Also, in many high power applications, such as for many battery charging circuits, the DCR of the inductor may be on the order of mΩ range, which would require large inductor current (e.g., greater than 1 A, 10 A or more) to enable some reasonable measurement of the DCR. This is not practical to implement on-chip or on board as would be required to implement many existing types of inductor identification methods.

As used herein, the term "circuit" can include a collection of active and/or passive elements that perform a circuit function, such as an analog circuit and/or digital circuit. Additionally or alternatively, for example, the term "circuit" can include an integrated circuit (IC) where all or some of the circuit elements are fabricated on a common substrate (e.g., semiconductor substrate, such as a die or chip) or a system-on-chip within a common package. For example, circuitry of a power converter (e.g., the control circuit 106, including time control circuit 122 and DCR control circuit 132, etc.) can be implemented on a semiconductor substrate. Additionally, the term "couple" is used throughout the specification. The term may cover connections, communications, or signal paths that enable a functional relationship consistent with this description. For example, if device A generates a signal to control device B to perform an action, in a first example device A is coupled to device B, or in a second example device A is coupled to device B through intervening component C if intervening component C does not substantially alter the functional relationship between device A and device B such that device B is controlled by device A via the control signal generated by device A.

Modifications are possible in the described embodiments, and other embodiments are possible, within the scope of the claims.

What is claimed is:

1. A device comprising:
   a first circuit configured to be coupled to an inductor, the first circuit including a second circuit configured to be tuned;
   a third circuit coupled to the second circuit, the third circuit configured to tune the second circuit;
   a fourth circuit coupled to the first circuit;
   a fifth circuit coupled to the fourth circuit, the fifth circuit configured to output to the fourth circuit a gain adjust signal responsive to an average current of the inductor; and
   a sixth circuit coupled to the fourth circuit, the sixth circuit configured to control current in the inductor based on the gain adjust signal.

2. The device of claim 1, wherein:
   the third circuit is configured to tune the second circuit based on a zero crossing of a signal representative of a current of the inductor.

3. The device of claim 1, wherein:
   the first circuit includes:
   a differential amplifier with a first input, a second input, a first output, and a second output;
   a first resistor including a first terminal configured to be coupled to a first terminal of the inductor, and a second terminal coupled to the first input of the differential amplifier;
   a second resistor including a first terminal configured to be coupled to a second terminal of the inductor, and a second terminal coupled to the second input of the differential amplifier;

a first current source coupled to the second terminal of the first resistor;
a second current source coupled to the second terminal of the second resistor;
a first transistor including a control terminal coupled to the first output of the differential amplifier, a first terminal, and a second terminal coupled to the first current source; and
a second transistor including a control terminal coupled to the second output of the differential amplifier, a first terminal, and a second terminal coupled to the second current source.

4. The device of claim 3, wherein:
the first circuit includes:
a first current mirror coupled to the first transistor;
a second current mirror coupled to the second transistor;
a third current source coupled to the first current mirror;
a fourth current source coupled to the second current mirror;
a first output of the first circuit coupled to the first current mirror; and
a second output of the first circuit coupled to the second current mirror.

5. The device of claim 4, wherein:
the second circuit includes a third resistor coupled in parallel with an adjustable capacitor.

6. The device of claim 5, wherein:
a first terminal of the third resistor and a first terminal of the adjustable capacitor are coupled to the first output of the first circuit; and
a second terminal of the third resistor and a second terminal of the adjustable capacitor are coupled to the second output of the first circuit.

7. The device of claim 1, wherein:
the sixth circuit includes:
a pulse width modulation comparator including a first input coupled to an output of the fifth circuit, a second input, and an output; and
a ramp circuit coupled to the second input of the pulse width modulation comparator.

8. The device of claim 7, further comprising:
a drive circuit coupled to the output of the pulse width modulation comparator.

9. The device of claim 8, wherein:
the drive circuit includes a plurality of gate drivers coupled to respective gates of a respective plurality of transistors; and
the respective plurality of transistors is configured to control current through the inductor.

10. The device of claim 1, wherein:
the fifth circuit includes:
a first gain circuit including a first input coupled to the first circuit, a second input, and an output;
a comparator including a first input configured to receive an average current of the inductor, a second input, and an output coupled to the second input of the first gain circuit; and
a second gain circuit including an input configured to receive a reference voltage signal, a first output coupled to the second input of the comparator, and a second output coupled to the output of the first gain circuit.

11. The device of claim 10, wherein:
the first gain circuit includes a logic circuit.

12. The device of claim 1, wherein:
the fifth circuit includes:
a first gain circuit including a first input coupled to the first circuit and an output;
a second gain circuit including a first input configured to receive an average current of the inductor, a second input, and an output coupled to the output of the first gain circuit; and
a third gain circuit including an input configured to receive a reference voltage signal, a first output coupled to the second input of the second gain circuit, and a second output coupled to the output of the first gain circuit.

13. The device of claim 12, wherein:
the second gain circuit includes a filter.

14. The device of claim 13, wherein:
the filter is configured to reduce high-frequency components of a signal on the output of the second gain circuit.

15. An integrated circuit comprising:
a first circuit including inputs and an output, the inputs of the first circuit adapted to be coupled to terminals of an inductor, the first circuit including a second circuit coupled between the inputs and the output of the first circuit;
a third circuit including an input and an output, the input of the third circuit adapted to be coupled to a high-side terminal of the inductor, and the output of the third circuit coupled to the second circuit;
a fourth circuit including a first input, a second input, and an output, the first input coupled to the output of the first circuit;
a fifth circuit including a first input, a second input, and an output, the first input of the fifth circuit adapted to be coupled to a first voltage, the output of the fifth circuit coupled to the second input of the fourth circuit;
a sixth circuit including a first input, and an output, the first input of the sixth circuit coupled to the output of the fourth circuit, and the output of the sixth circuit adapted to drive a current in the inductor; and
a seventh circuit including an input, a first output, and a second output, the input adapted to be coupled to a voltage, the first output coupled to the second input of the fifth circuit, and the second output coupled to the second input of the fourth circuit.

16. The integrated circuit of claim 15, wherein:
the first circuit is adapted to provide a representative voltage of a current through the inductor;
the second circuit includes a resistor and a variable capacitor;
the third circuit is adapted to adjust a value of the variable capacitor;
the fourth circuit is adapted to set a gain;
the fifth circuit is adapted to output a gain control signal at the output;
the sixth circuit is adapted to activate a switch device; and
the seventh circuit is adapted to determine an average current through the inductor.

17. The integrated circuit of claim 15, wherein:
the third circuit includes:
a first zero crossing detector having an input and an output, in which the input is coupled to the output of the first circuit;
a second zero crossing detector having an input and an output, in which the input is adapted to be coupled to a high-side terminal of the inductor; and a logic circuit having first and second logic inputs and a logic output, the first and second logic inputs coupled to respective outputs of the first and second zero crossing detectors, the logic output coupled to a control input of the second circuit.

18. The integrated circuit of claim 15, wherein:

the third circuit is configured to tune the second circuit responsive to a zero crossing of a signal at the output of the first circuit matching a zero crossing of a signal representative of the current in the inductor, and the fifth circuit is configured to provide a gain adjust signal at the output of the fifth circuit responsive to a signal representative of average inductor current and a current command signal.

19. A system comprising:

a first circuit including an inductor; and a second circuit including:

a current sensor having inputs and an output, the inputs of the current sensor coupled to terminals of the inductor, the current sensor including tunable time constant circuit coupled between the inputs of the current sensor and the output of the current sensor;

an average current sense circuit having an input and output, in which the input is coupled to one of a power input and a power output;

a first gain circuit having an input coupled to the output of the current sensor; and     a control circuit having first and second control inputs and an output, the first control input coupled to the output of the average current sense circuit, the second control input coupled to an output of a second gain circuit, the output of the control circuit coupled to an input of the first gain circuit.

20. The system of claim 19, wherein:

the second circuit includes a switch control circuit configured to control a current through the inductor; and the second circuit includes an input coupled to an output of the first gain circuit.

\* \* \* \* \*